(12) United States Patent
Mathias et al.

(10) Patent No.: US 6,632,201 B1
(45) Date of Patent: Oct. 14, 2003

(54) LOCKING NEEDLE PROTECTOR

(75) Inventors: Jean-Marie Mathias, Lillois (BE); Philippe Van Heems, La Chatre (FR); Gianni Di Stefani, Villers-St-Amand (BE); Thomas Walter Coneys, Saint-Doulchard (FR)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/442,210

(22) Filed: Nov. 17, 1999

(51) Int. Cl.⁷ .................................................. A61M 5/00

(52) U.S. Cl. .................. 604/263; 604/198; 604/164.08; 604/162

(58) Field of Search ..................... 604/164.07, 164.08, 604/198, 110, 263, 192, 162, 165.02, 165.03, 250, 264

(56) References Cited

U.S. PATENT DOCUMENTS

| | | |
|---|---|---|
| 2,857,912 A | 10/1958 | Feinstone et al. |
| 3,323,523 A | 6/1967 | Scislowicz et al. |
| 3,568,673 A | 3/1971 | Cowley |
| 3,572,334 A | 3/1971 | Petterson |
| 3,595,230 A | 7/1971 | Suyeoka et al. |
| 3,610,240 A | 10/1971 | Harautuneian |
| RE27,797 E | 10/1973 | Sorenson et al. |
| 3,910,272 A | 10/1975 | Forberg |
| 4,068,659 A | 1/1978 | Moorehead |
| 4,170,993 A | 10/1979 | Alvarez |
| 4,329,989 A | 5/1982 | Dallons et al. |
| 4,417,887 A | 11/1983 | Koshi |
| 4,425,120 A | 1/1984 | Sampson et al. |
| 4,573,976 A | 3/1986 | Sampson et al. |
| 4,631,057 A | 12/1986 | Mitchell |
| 4,631,058 A | 12/1986 | Raines |
| 4,643,722 A | 2/1987 | Smith, Jr. |
| 4,664,654 A | 5/1987 | Strauss |
| 4,676,783 A | 6/1987 | Jagger et al. |
| 4,693,708 A | 9/1987 | Wanderer et al. |
| 4,731,059 A | 3/1988 | Wanderer et al. |
| 4,735,618 A * | 4/1988 | Hagen ........................ 604/192 |
| 4,737,143 A | 4/1988 | Russell |
| 4,747,836 A | 5/1988 | Luther |
| 4,790,828 A | 12/1988 | Dombrowski et al. |
| 4,820,282 A | 4/1989 | Hogan |

(List continued on next page.)

FOREIGN PATENT DOCUMENTS

| | | |
|---|---|---|
| CA | 729419 | 3/1966 |
| EP | 0 265 159 A2 | 4/1988 |
| EP | 0 353 916 A1 | 7/1990 |
| EP | 0 425 448 A2 | 2/1991 |
| EP | 0 459 953 A1 | 4/1991 |
| EP | 0 475 857 A1 | 3/1992 |
| EP | 0 664 139 B1 | 7/1995 |
| EP | 0 830 871 A2 | 3/1998 |
| EP | 00 97 8465 | 12/2002 |
| FR | 2 263 789 | 3/1974 |
| WO | WO 90/03196 | 4/1990 |
| WO | WO 92/11885 | 7/1992 |
| WO | WO 95/24232 | 9/1995 |
| WO | WO 99/12594 | 9/1998 |
| WO | WO 98/58584 A1 | 12/1998 |
| WO | WO 00/06225 | 2/2000 |

OTHER PUBLICATIONS

Abstract of Japanese Patent Application No. 63–036413 (JP 8836413), Filed Feb. 18, 1988.

*Primary Examiner*—Brian L. Casler
*Assistant Examiner*—Jennifer Maynard
(74) *Attorney, Agent, or Firm*—Andrew Kolomayets; Michael C. Mayo

(57) ABSTRACT

Needle protectors for retaining needles are disclosed. The needle protector includes a housing with an opening at each of a proximal and distal end. The needle protector may include a portion that is depressible to a substantially fixed position over the needle retracted within the housing.

16 Claims, 4 Drawing Sheets

U.S. PATENT DOCUMENTS

| | | | | |
|---|---|---|---|---|
| 4,840,613 A | | 6/1989 | Balbierz | |
| 4,840,619 A | | 6/1989 | Hughes | |
| 4,842,587 A | | 6/1989 | Poncy | |
| 4,867,172 A | * | 9/1989 | Haber et al. | 128/763 |
| 4,874,383 A | | 10/1989 | McNaughton | |
| 4,888,001 A | | 12/1989 | Schoenberg | |
| 4,917,243 A | | 4/1990 | Abrams et al. | |
| 4,923,445 A | | 5/1990 | Ryan | |
| 4,927,019 A | | 5/1990 | Haber et al. | |
| 4,927,415 A | | 5/1990 | Brodsky | |
| 4,929,241 A | | 5/1990 | Kulli | |
| 4,932,940 A | | 6/1990 | Walker et al. | |
| 4,935,011 A | | 6/1990 | Hogan | |
| 4,935,012 A | | 6/1990 | Magre et al. | |
| 4,941,881 A | | 7/1990 | Masters et al. | |
| 4,943,284 A | | 7/1990 | Erlich | |
| 4,946,447 A | | 8/1990 | Hardcastle et al. | |
| 4,994,046 A | | 2/1991 | Wesson et al. | |
| 5,013,305 A | | 5/1991 | Opie et al. | |
| 5,030,212 A | | 7/1991 | Rose | |
| 5,061,250 A | | 10/1991 | Shields | |
| 5,069,341 A | | 12/1991 | Barbieri et al. | |
| 5,085,639 A | | 2/1992 | Ryan | |
| 5,088,982 A | | 2/1992 | Ryan | |
| 5,092,461 A | | 3/1992 | Adam | |
| 5,098,403 A | | 3/1992 | Sampson | |
| 5,108,376 A | | 4/1992 | Bonaldo | |
| 5,112,311 A | | 5/1992 | Utterberg et al. | |
| 5,112,313 A | | 5/1992 | Sallee | |
| 5,120,320 A | | 6/1992 | Fayngold | |
| 5,137,515 A | | 8/1992 | Hogan | |
| 5,137,519 A | | 8/1992 | Littrell et al. | |
| 5,154,698 A | | 10/1992 | Compagnucci et al. | |
| 5,167,640 A | | 12/1992 | Balding | |
| 5,169,392 A | * | 12/1992 | Ranford et al. | 604/198 |
| 5,171,231 A | | 12/1992 | Heiliger | |
| 5,192,275 A | | 3/1993 | Burns | |
| 5,197,956 A | | 3/1993 | Brizuela | |
| RE34,223 E | | 4/1993 | Bonaldo | |
| 5,201,713 A | | 4/1993 | Rossetti | |
| 5,215,528 A | * | 6/1993 | Purdy et al. | 604/164 |
| 5,219,339 A | | 6/1993 | Saito | |
| 5,226,894 A | | 7/1993 | Haber et al. | |
| 5,266,072 A | | 11/1993 | Utterberg et al. | |
| 5,279,588 A | | 1/1994 | Nicoletti et al. | |
| 5,290,264 A | | 3/1994 | Utterberg | |
| 5,312,368 A | | 5/1994 | Haynes | |
| 5,330,438 A | | 7/1994 | Gollobin et al. | |
| 5,346,475 A | | 9/1994 | Gregorio | |
| 5,350,368 A | | 9/1994 | Shields | |
| 5,376,075 A | | 12/1994 | Haughton et al. | |
| 5,380,293 A | | 1/1995 | Grant | |
| 5,382,240 A | | 1/1995 | Lam | |
| 5,425,720 A | | 6/1995 | Rogalsky et al. | |
| 5,433,703 A | | 7/1995 | Utterberg et al. | |
| 5,486,163 A | | 1/1996 | Haynes | |
| 5,498,244 A | * | 3/1996 | Eck | 604/198 |
| 5,498,245 A | | 3/1996 | Whisson | |
| 5,505,711 A | | 4/1996 | Arakawa et al. | |
| 5,520,654 A | | 5/1996 | Wahlberg | |
| 5,545,146 A | | 8/1996 | Ishak | |
| 5,549,558 A | | 8/1996 | Martin | |
| 5,549,571 A | | 8/1996 | Sak | |
| 5,549,572 A | | 8/1996 | Byrne et al. | |
| 5,562,636 A | | 10/1996 | Utterberg | |
| 5,562,637 A | | 10/1996 | Utterberg | |
| 5,573,512 A | | 11/1996 | van den Haak | |
| 5,584,813 A | | 12/1996 | Livingston et al. | |
| 5,601,536 A | * | 2/1997 | Crawford et al. | 604/263 |
| 5,704,917 A | | 1/1998 | Utterberg | |
| 5,704,924 A | | 1/1998 | Utterberg | |
| 5,718,688 A | * | 2/1998 | Wozencroft | 604/164 |
| 5,746,215 A | | 5/1998 | Manjarrez | |
| 5,749,859 A | * | 5/1998 | Powell | 604/167 |
| 5,772,638 A | | 6/1998 | Utterberg et al. | |
| 5,800,400 A | | 9/1998 | Hogan | |
| 5,827,239 A | | 10/1998 | Dillon et al. | |
| 5,833,670 A | | 11/1998 | Dillon et al. | |
| 5,879,337 A | | 3/1999 | Kuracina et al. | |
| 5,899,886 A | | 5/1999 | Cosme | |
| 5,910,132 A | * | 6/1999 | Schultz | 604/162 |
| 5,925,032 A | | 7/1999 | Clements | |
| 5,951,523 A | | 9/1999 | Osterlind et al. | |
| 5,951,529 A | | 9/1999 | Utterberg | |
| 6,042,570 A | | 3/2000 | Bell et al. | |

* cited by examiner

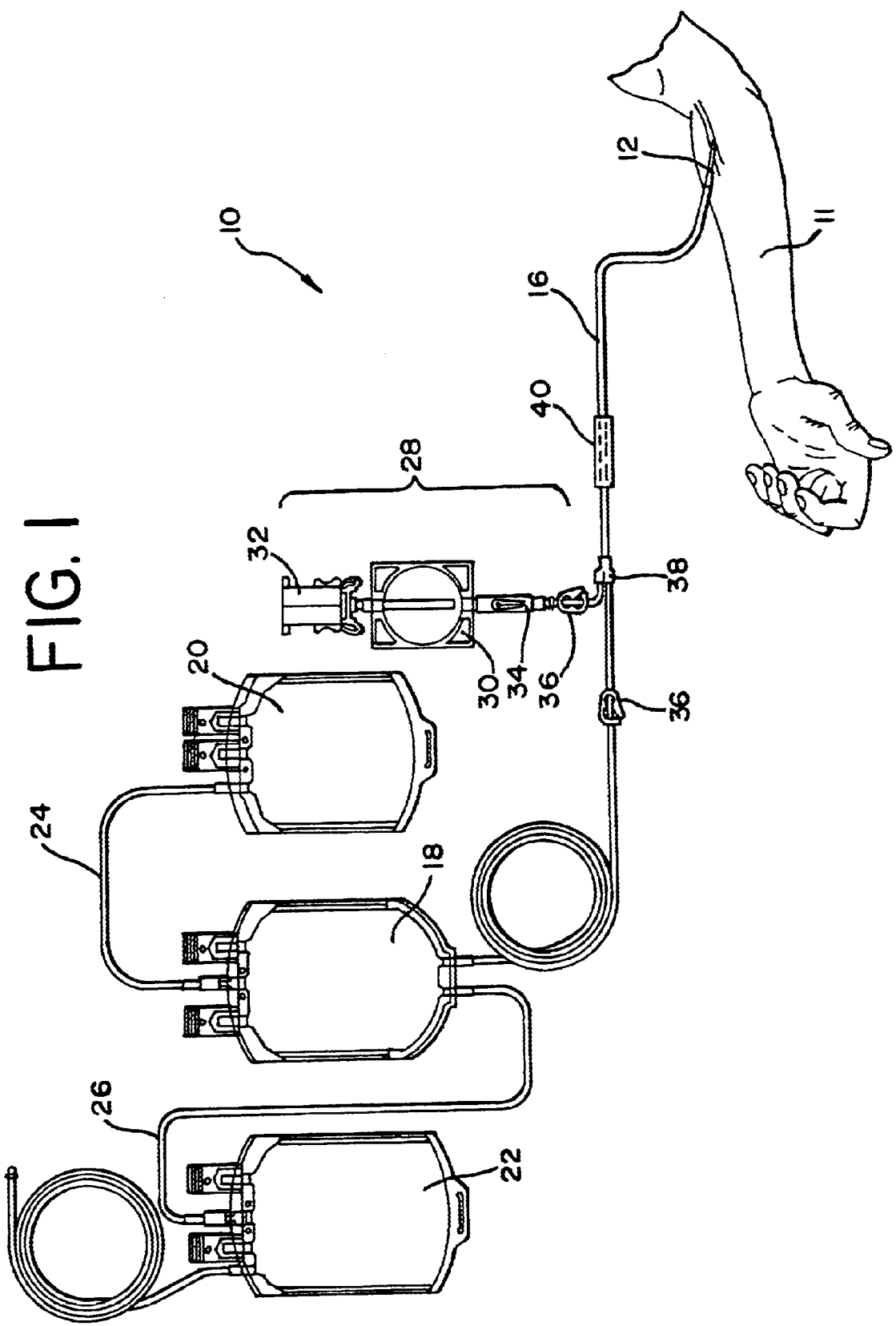

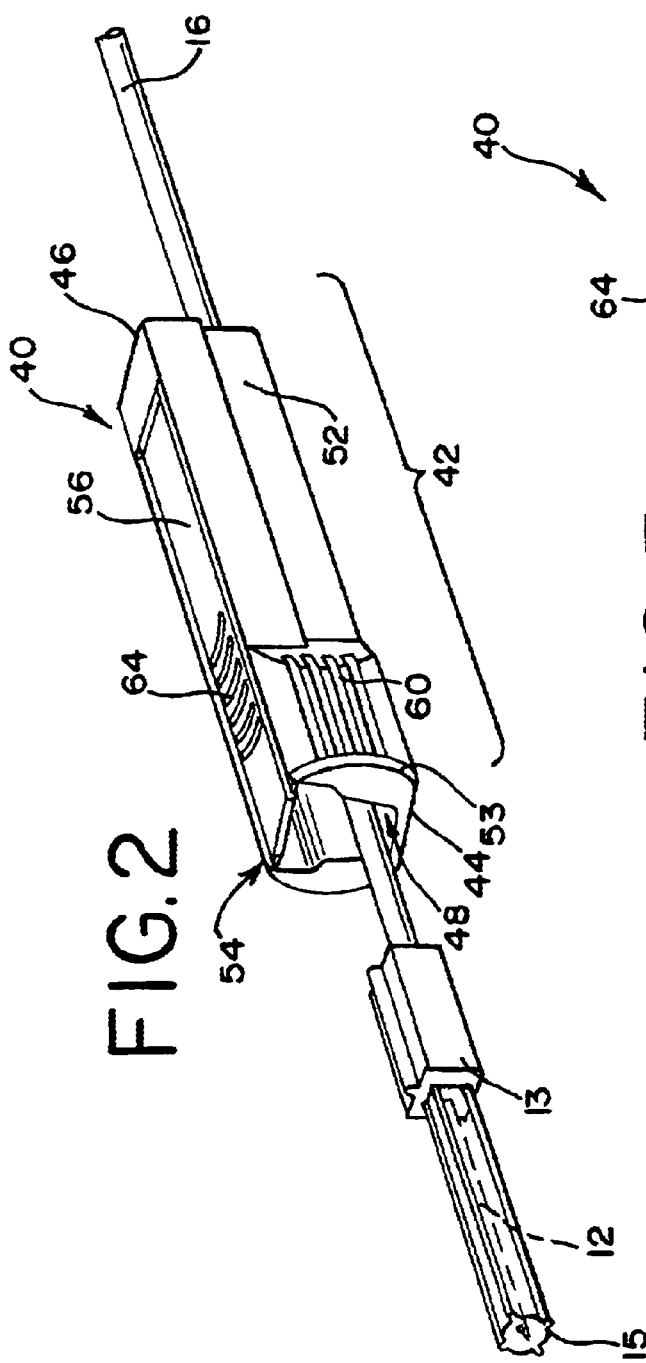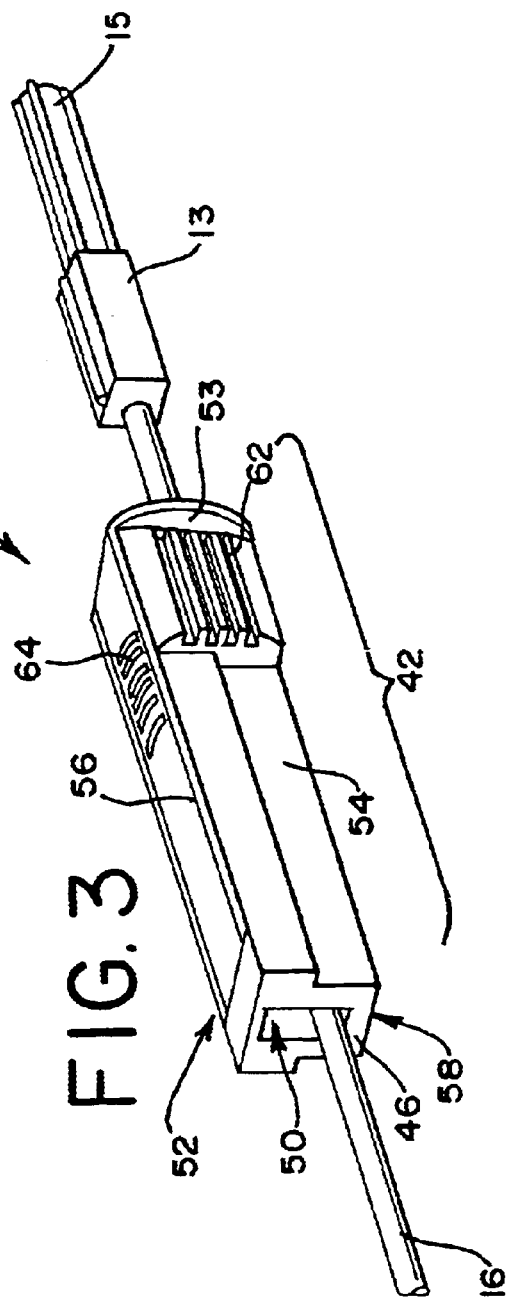

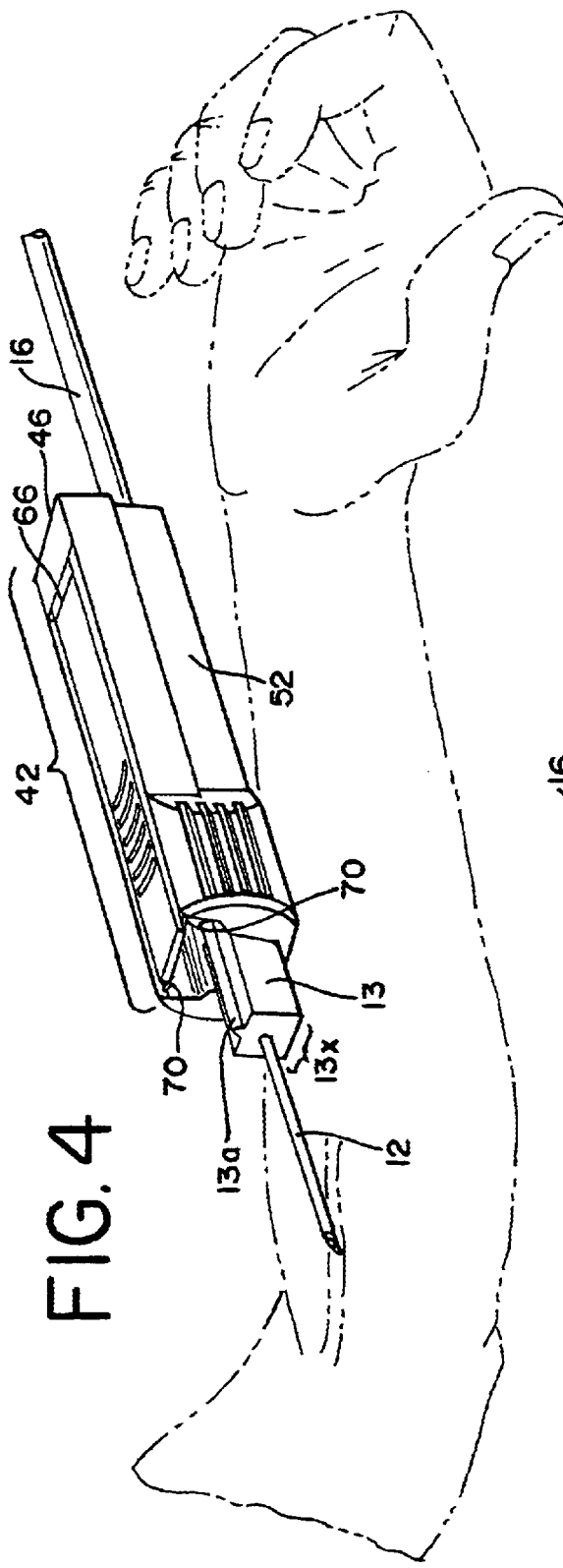
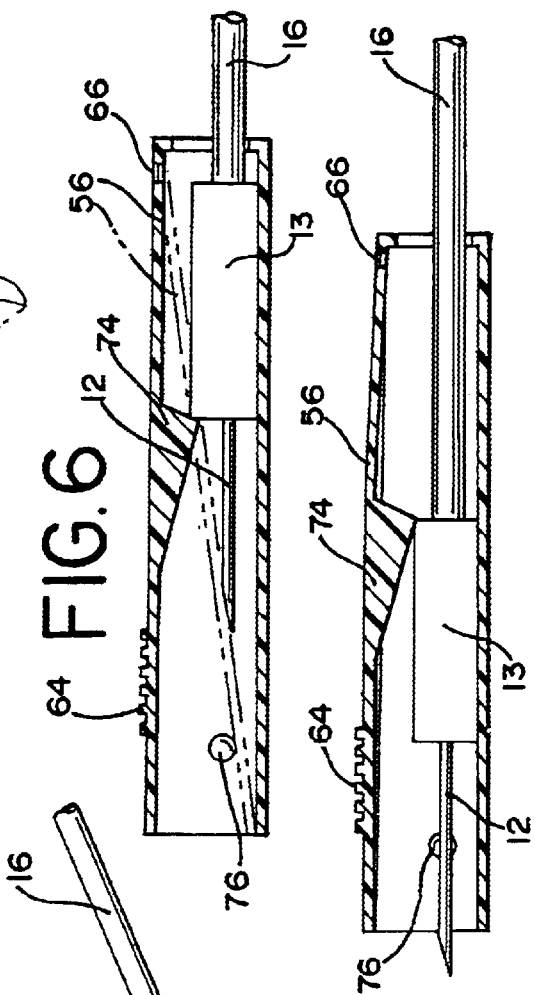
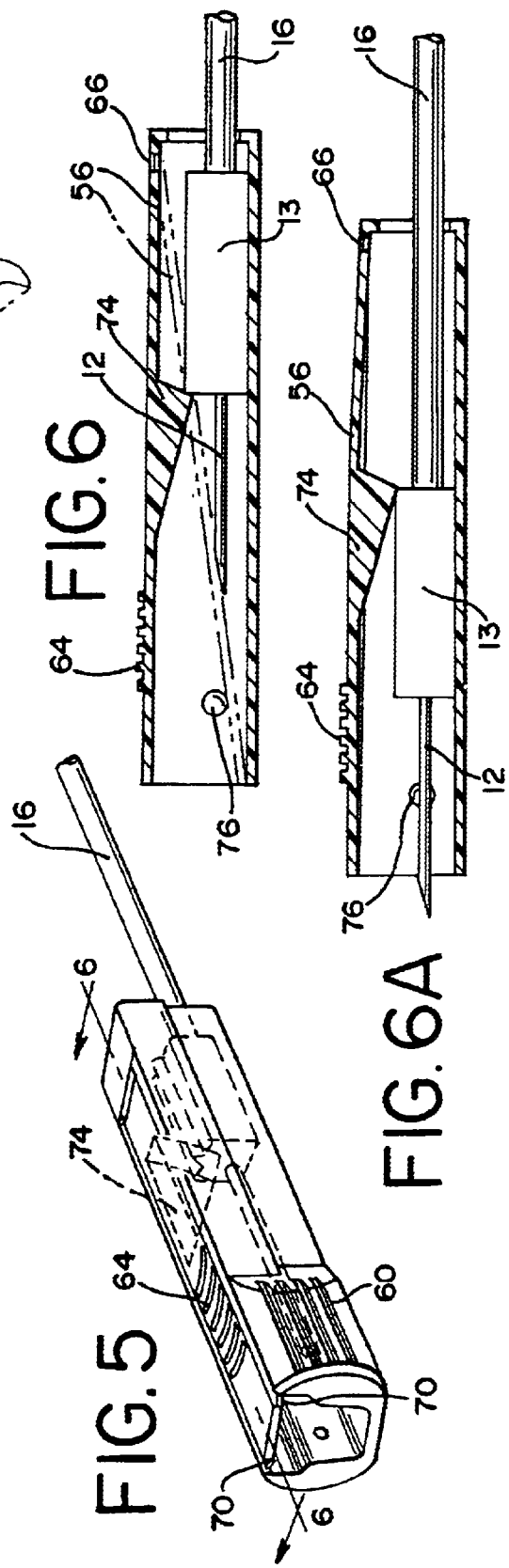

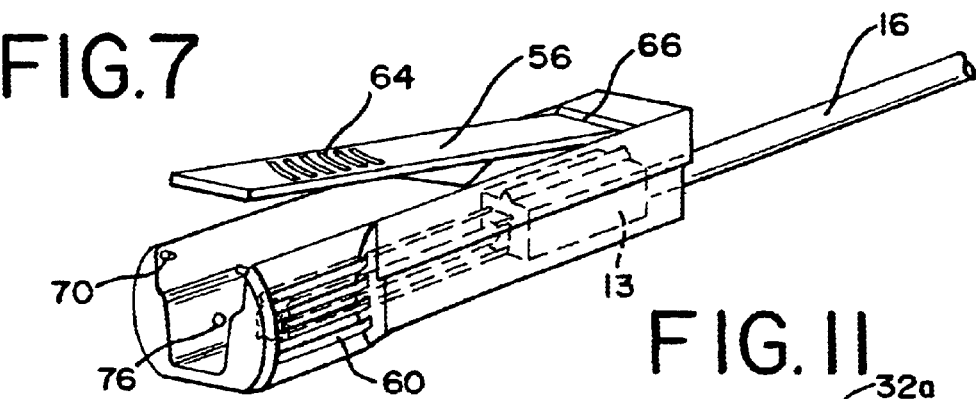
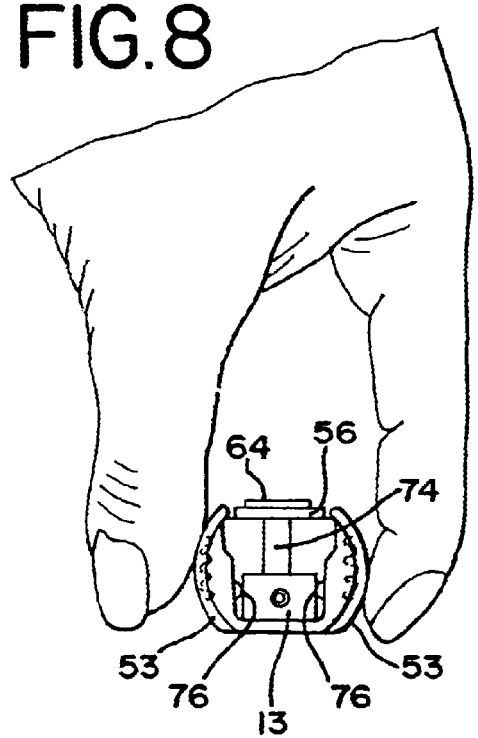
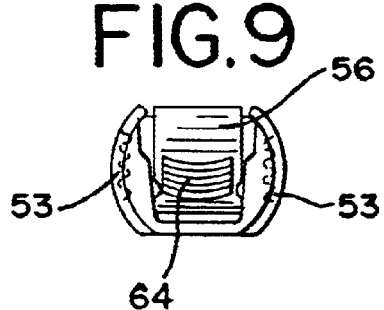
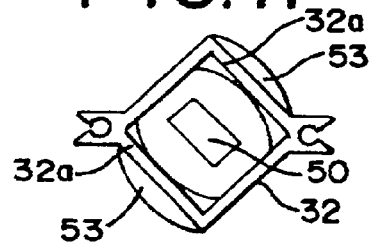
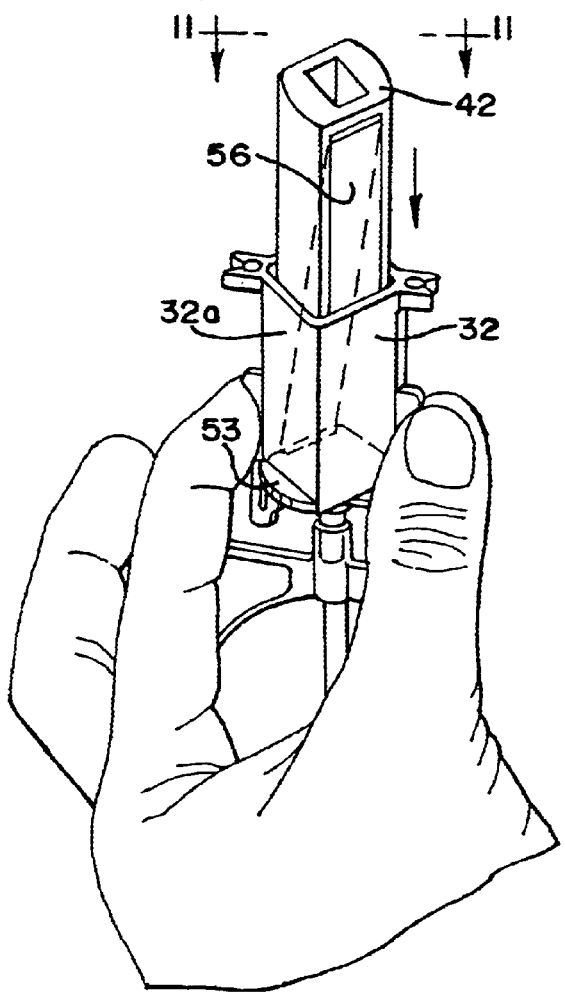

LOCKING NEEDLE PROTECTOR

The present invention relates generally to protective devices for used medical needles to prevent inadvertent user contact with such needles. The protective devices (i.e., needle protectors) of the present invention may be incorporated into a disposable plastic tubing and container set used in the collection and processing of a biological fluid such as blood.

BACKGROUND OF THE INVENTION

Needles are used in a wide variety of procedures in the medical field. For example, needles are commonly used to administer fluids, such as intravenous solution, medication, blood components and the like to patients, as well as to withdraw fluids, such as blood or other fluids from patients or donors. One very common application for needles is in collecting blood from a donor.

Withdrawing blood from a donor typically involves inserting a needle into the donor's vein and withdrawing blood from the donor through the needle and associated plastic tubing into a collection bag or blood processing device. Typically, the needle, tubing and containers make up a blood processing set which is disposed of after a single use.

The presence of blood-borne pathogens that may lead to serious medical conditions such as hepatitis, AIDS and other diseases have given rise to increased concern for accidental needle puncture after a needle is withdrawn from a patient's or donor's arm. The concern includes withdrawal of the needle and the possibility of an accidental needle stick to the technician or nurse, as well as the safe disposal of the used needle. For this reason, the medical field has developed devices that allow for the safe withdrawal and storage of the used needles.

Some of the early needle protectors were in the form of a cap that was placed over the needle. The caps typically included a flat plate or shield, which extended radially outwardly near the opening of the cap. The shield protected the technician's fingers from the needle during placement of the cap over the needle. A needle protector of this type is described in U.S. Pat. No. 4,840,618.

More recently, in the field of blood processing and/or collection, the needle protectors have been incorporated into the disposable tubing and container sets used to collect and process the blood. For example, U.S. Pat. No. 5,833,670 discloses a sheath adapted to be slidably supported on the tubing of the disposable processing set. The sheath is open at its distal and proximal ends with the tubing extending through the open ends of the protective sheath. After collection, the sheath is slidably moved over the needle and/or the needle is completely retracted within the sheath.

U.S. Pat. No. 5,772,638 discloses a needle protector having slotted side walls (to receive a winged needle) and an end wall. The protector is slidably mounted on the tubing of the disposable processing set. As the protector is slidably moved forward over the needle (and the needle is withdrawn into the protector) the end wall causes the needle and the hub to be held in the sheath in an acute angle to the top wall with the needle tip positioned against the underside of the top wall.

While these needle protectors have generally worked satisfactorily, efforts continue to provide further improvements in the area of needle protection.

SUMMARY OF THE INVENTION

The present invention is generally directed to a needle protector having an elongated housing that has a distal end and a proximal end. The housing defines a needle-receiving compartment that restricts unintentional contact with the needle. The housing further includes an opening at each of the proximal and distal ends and is adapted to receive a needle through the opening at the distal end. The housing includes a portion that is depressible to a substantially fixed position to capture a needle within the housing.

In a further aspect of the present invention, the needle protector may include a depressible top wall hingedly attached to the housing at the proximal end. In another aspect of the present invention, the needle protector may include at least a pair of facing side walls. The side walls may be adapted to maintain the top wall in the depressed position. In another aspect of the present invention, the needle protector may include a detent extending from the interior surface of at least one of the walls, such as the top wall, to immobilize the retracted needle.

The present invention is also directed to a needle and a needle protector assembly. The assembly includes a needle mounted on a hub and a length of tubing having one end attached to the hub, the tubing defining a flow path for a biological fluid. The assembly further includes a housing having a distal end and a proximal end. The housing defines a needle-receiving compartment that restricts unintentional contact with the needle. The housing may also include an opening at each of the proximal and distal ends. The length of tubing extends through at least the opening at the proximal end and allows for movement of the housing and tubing relative to one another. The housing includes a portion that is depressible to a substantially fixed position to capture a needle within the housing.

BRIEF DESCRIPTION OF THE DRAWINGS

FIG. 1 is a plan view of a disposable tubing and container set with a needle protector embodying the present invention;

FIG. 2 is a perspective view from the distal end of a needle protector embodying the present invention located on a tubing segment, with a needle at the end of a tubing segment;

FIG. 3 is a perspective view from the proximal end of the needle protector of FIG. 2;

FIG. 4 is a perspective view of the needle protector of FIG. 2 with the needle in a partially retracted position;

FIG. 5 is a perspective view of the needle protector of FIG. 2 with the needle in a completely retracted position;

FIG. 6 is a cross-sectional side view of the needle protector of FIG. 5 taken along lines 6-6;

FIG. 6A is a cross-sectional side view of the needle protector of FIG. 5 as the needle is being retracted into the needle-receiving compartment of the housing;

FIG. 7 is a perspective view of the needle protector with the needle disposed in a completely retracted position and the top wall detached from the housing at the distal end;

FIG. 8 is a distal end view of the needle protector of FIG. 5 with the needle disposed in a completely retracted position;

FIG. 9 is a distal end view of the needle protector of FIG. 8 with the top wall depressed over the needle;

FIG. 10 is a perspective view of the needle protector (with the top depressed) placed within a tube holder of the disposable processing set; and FIG. 11 is an end view of the needle protector disposed within the tube holder of FIG. 10.

DETAILED DESCRIPTION OF THE DRAWINGS

The needle protector of the present invention will be described below in the context of its preferred use, namely, as a needle protector for a needle that is part of a disposable tubing and container set intended for the collection and processing of blood. Of course, it will be understood that the needle protector of the present invention is not limited to use with a disposable tubing and container set or even to use in the medical field. The needle protector of the present invention may be used in any other application where a needle that is attached to a length of tubing is employed.

Also, as used herein, the term "needle" refers to any elongated member having a sharpened tip for puncturing or piercing. The term "needle" is not limited to traditional venipuncture needles which are typically made of stainless steel and are relatively small in diameter. Although the term "needle" includes such venipuncture needles, it also includes piercing members made from other materials, such as plastic, and includes cannulas, coupling devices and the like.

Turning now to the drawings, FIG. 1 shows a disposable tubing and container set 10, which is particularly suitable for use in the processing of blood from a donor 11. The illustrated disposable set 10 may include a needle such as venipuncture needle 12, and a plastic tubing segment 16 attached to needle 12 and extending from needle 12 to a plastic, blood collection container 18. The disposable blood processing set 10 may include a single blood collection container 18, or more commonly, as shown in FIG. 1, may include a primary container and additional, integrally attached containers 20 and 22, as is well known in the field.

Briefly, during use, primary container 18 (sometimes referred to as the donor bag) receives whole blood from donor 11 through tubing 16 and needle 12. Container 18 typically includes a suitable anticoagulant such as citrate phosphate dextrose (CPD), citrate phosphate dextrose adenine (CPDA) or acid citrate dextrose (ACD).

Containers 20 and 22 may be attached to primary container 18 by integrally attached transfer tubing 24 and 26. Containers 20 and 22 are provided to receive blood components such as, but not limited to, red blood cells and plasma that have been separated from whole blood. The methods and disposable sets for practicing such methods are well known and will not be discussed here. They are, however, described in U.S. Pat. Nos. 4,222,379 and 5,445,629, which are incorporated by reference herein.

Disposable processing set 10 may also include an integrally attached sampling system 28. Sampling system 28 includes a sampling pouch 30, a frangible connector 34 and a tube holder 32 for receiving a sampling vial. A sampling system 28 of the type shown in FIG. 1 (and the method of sampling) is described in co-pending U.S. application Ser. No. 09/364,628, filed Jul. 29, 1999 which is also incorporated by reference herein.

As shown in FIG. 1, blood processing set 10 also includes a needle protector 40 embodying the present invention. Turning now to FIGS. 2 and 3, the needle protector 40 of the present invention includes, in general, an elongated housing 42. Housing 42 has a distal end 44 and a proximal end 46. Housing 42 further includes an opening 48 at the distal end 44 and an opening 50 at proximal end 46. As shown in FIGS. 2 and 3, the tubing segment 16 extends through the open ends 48 and 50 of housing 42. A needle 12 mounted on hub 13 is attached to tubing 16. Needle 12 may be enclosed within cover 15 which is removed at the time of use.

In a preferred embodiment housing 42 is defined by side walls 52 and 54, top wall 56, and bottom wall 58 to provide a needle-receiving compartment. As shown in FIG. 2 and 3, side walls 52 and 54 may include flanges 53 at the distal end 44 of housing 42. In an alternative embodiment, housing 42 may be defined by top wall 56 and a continuous, arcuate wall that extends from one side of top wall 56 to the other side. In another alternative embodiment, housing 42 may be defined by a top wall and two side walls to provide, for example, a needle-receiving compartment with a substantially triangular cross-section.

Housing 42 may be made by casting, injection molding or other techniques known to those of skill in the art. Housing 42 may be made of any material suitably rigid and puncture resistant and suitable for use in the medical field. For example, housing 42 may be made of any thermoplastic material that can be sterilized by known sterilization techniques including, but not limited to autoclaving, gamma radiation, or an electron beam radiation. Housing 42 may be made (by, for example, molding) of a polyolefin material, such as, most preferably, polypropylene. Other suitable materials may include polyethylene, such as high density polyethylene, polyacetal and polycarbonate. It will be understood that the housing may also be made of blends of two or more materials, including the materials identified above.

As shown in FIGS. 2–4, housing 40 includes gripping surfaces in the form of raised ribs 60 and 62 on the outer surfaces of side walls 52 and 54, and on the outer surface of the top wall 56. Gripping surfaces 60, 62 and 64 may be formed during the molding process in ways that will be understood by those of skill in the art. Where housing includes bottom wall 58, such wall 58 may have a substantially smooth exterior surface.

Turning briefly to FIG. 7, top wall 56 is hinged to the housing at proximal end 46. Hinge 66 may be a section of top wall 56 which has a reduced thickness relative to the remainder of top wall 56. For example, whereas top wall 56 (or any other wall housing 42) may have a thickness of approximately 1.0 to 1.5 mm, the thickness of hinge 66 may be approximately 0.2 to 0.4 mm.

Top wall 56 may be attached to housing 42 at distal end 44 by frangible tabs or webs 70. By depressing distal end 44 and top wall 56, frangible tabs or webs 70 may be broken and, as more specifically shown by the broken lines in FIG. 6, top wall 56 may be depressed to a location between side walls 52 and 54 and over a needle retracted within housing 42. In a preferred embodiment, tabs or webs 70 are thin sections of plastic, molded with housing 42. Also, in the event that needle 12 becomes inadvertently fully retracted and captured within housing 42 prior to its use, breakable tabs allow top wall 56 to be released from housing 42 and permit withdrawal of needle 12 for its intended use. Thus, an unused needle and needle protector assembly or unused disposable processing set where needle 12 is fully retracted would still be usable.

The needle protector may be slidably moved over tubing 16 and over needle 12 and hub 13. Needle 12 with needle hub 13 may be either partially or completely retracted within the housing 42 through distal opening 48. For example, FIG. 4 shows the needle in a partially retracted position. Most typically, needle 12 is inserted into the donor's vein such that rib 13a on hub 13 is turned away from the donor's arm, as shown in FIG. 4. However, during blood collection, it is not uncommon for the nurse or technician to rotate the needle 12 to, for example, improve blood flow, and change the orientation of hub 13. Thus, hub may be rotated 90° (in either direction) or 180° relative to the position shown in FIG. 4. It is also not uncommon for the nurse or technician to rotate housing 42 relative to the needle 12 and hub 13. For example, the technician may rotate housing 42 so that top wall 56 rests on and is in contact with the donor's arm. This provides a smooth surface (i.e., bottom wall 58) over which adhesive tape, used to hold housing 42 in place on the donor's arm, may be affixed. Accordingly, distal opening 48 should have a height and width sufficient to receive needle 12 and hub 13 regardless of whether hub 13 is retracted in its typical orientation or any of the above described orientations.

As shown in FIG. 2, opening 48 may be wider near the top wall and, preferably, tapers to a narrower width near bottom wall 58. A gradual, tapered transition from greater to smaller width of opening 48 is preferred to allow for easier depression of top wall 56, as described below. In any event, distal opening 48 near bottom wall 58 should be at least as wide and, preferably slightly wider, than the widest portion of hub 13 which is designated by reference numeral 13x in, for example, FIG. 4.

Needle 12 with needle hub 13 may be completely retracted within housing 42 as shown in FIGS. 5 and 6. Housing 42 allows for capture of needle 12 within the protector and for further shielding the retracted needle 12 from the outside environment. For example, as shown in FIG. 5, needle 12 (with hub 13) may be fully retracted and more permanently captured by the needle protector. As further shown in FIGS. 5 and 6, top wall 56 may include a detent 74 which depends from the inner surface of top wall 56. Of course, side walls 52, 54 and bottom wall 58 may also include detents or the like for retaining hub 13.

In any event, as housing 42 is slidably moved over needle 12 (or needle 12 is retracted into housing 42, needle hub 13 pushes detent 74 causing top wall 56 to slightly flex upwardly as shown in FIG. 6A. The degree of flexing will depend on whether, during retraction, hub 13 is in its normal orientation or turned 90° or 180° as described above. Once hub 13 has moved beyond detent 74, top wall 56 returns to its position and detent 74 prevents further forward movement (i.e., movement toward the distal end) of the needle 12. Further movement of the needle assembly in a rearward direction (i.e., movement toward the proximal end) through the opening 50 in proximal end 46 is also prevented as opening 50 is sized to. prevent passage of hub 13. In any event, the needle 12 is immobilized and reduces the risk that the technician will be injured by an accidental needle stick. Housing 42 is longer than the needle and hub so that distal end 44 of housing 42 is spaced far enough beyond the needle end to prevent inadvertent contact with the technician or other medical personnel.

To further secure the needle 12, top wall 56 may be depressed and "locked" over retracted needle 12. By applying pressure to top wall 56 (at, for example, gripping surfaces 64), tabs or webs 70 may be broken to allow depression of top wall 56. In a preferred embodiment, top wall 56 may be maintained and locked in this position. Thus, housing 42 may include means for capturing top wall and retaining top wall 56 in the depressed and locked position. In one embodiment, the capturing means may be bumps or protrusions 76 on the interior surfaces of side walls 52 and 54, as shown in FIG. 7. The protrusions 76 may be formed during the molding process or may be separately attached to the interior wall surfaces. As top wall 56 is depressed past protrusions 76, an audible "click" may be heard which assures the technician that top wall 56 is locked in the depressed position.

For further safety, where needle protector 40 of the present invention is part of a disposable tubing and container set such as the set shown in FIG. 1 and described in detail in U.S. patent application Ser. No. 09/364,628, filed Jul. 29, 1999 which has been incorporated by reference. With reference to FIG. 10, housing 42 with the needle 12 disposed therein (not shown) may be placed inside a tube holder 32 for disposal with the entire disposable set. Housing 42 may be inserted into open tube holder 32, distal end 44 first. Housing 42 is advanced through the open holder so that the distal end 44 exits through the opposite open end of holder 32. Removal of housing 42 from holder 32 is, in large part, prevented by flanges 53 which extend beyond the side walls 32a of holder 32 as shown in FIGS. 10 and 11. In other words, distal end 44 (and, more particularly, flanges 53) of housing 42 is held by the side walls 32a of the holder.

The present invention has been described in accordance with the preferred embodiment. However, it will be understood that minor variations to the embodiments shown herein may be made without departing from the present invention which is specifically set forth in the appended claims.

That which is claimed:

1. A needle protector for use with a blood processing set of the type that includes a flexible plastic tube terminating in a needle hub and a needle mounted on said hub, wherein said protector is slidably moveable along said plastic tube, said protector comprising:

an elongated housing defined by at least a pair of facing side walls, said housing comprising an open distal end, an open proximal end, and a depressible wall frangibly attached to said housing at said distal end and hingedly attached to said housing at a location proximally spaced from said distal end;

wherein at least one of said side walls includes an interior surface comprising a retaining member extending from said surface for retaining said depressible wall in a depressed position and thereby shielding a retracted needle.

2. The needle protector of claim 1 comprising said pair of facing side walls, a bottom wall and a depressible top wall.

3. The needle protector of claim 1 wherein said depressible wall is frangibly attached to said housing by breakable tabs.

4. The needle protector of claim 2 wherein said walls comprise inner and outer surfaces, wherein at least one of said walls comprises gripping means on its outer surface.

5. The needle protector of claim 4 wherein said gripping means comprise raised ribs.

6. The needle protector of claim 4 wherein said inner surface of at least one of said walls comprises a detent extending therefrom.

7. The needle protector of claim 6 wherein said detent depends from said top wall.

8. The needle protector of claim 2 wherein said distal end is open, said opening being wider near said top wall than near said bottom wall.

9. The needle protector of claim 1 wherein said housing is made of a thermoplastic material.

10. The needle protector of claim 1 wherein said housing is made of a material selected from the group consisting of polypropylene and polyethylene.

11. The needle protector of claim 10 wherein said polyethylene comprises a high density polyethylene.

12. The needle protector of claim 1 wherein said open distal end is adapted to receive a needle assembly comprising a needle mounted on a hub, wherein said distal opening is of a size sufficient to receive said hub and said proximal opening is of a size sufficient to prevent passage of said hub through said open proximal end.

13. The needle protector of claim 12 wherein said distal end opening is of a fixed size during movement of said hub into said housing.

14. The needle protector of claim 1 wherein said depressible wall is hingedly attached to said housing at said proximal end.

15. The needle protector of claim 2 wherein each of said side walls includes an outwardly extending flange at said distal end of said housing.

16. The needle protector of claim 1 wherein each of said facing side walls comprises means for capturing and retaining said top wall in a depressed and locked position.

* * * * *